United States Patent [19]

Karanewsky et al.

[11] 4,416,833
[45] Nov. 22, 1983

[54] SUBSTITUTED CARBONYL PHOSPHINYL-ALKANOYL COMPOUNDS

[75] Inventors: Donald S. Karanewsky, Princeton Junction; Edward W. Petrillo, Jr., Pennington, both of N.J.

[73] Assignee: E. R. Squibb & Sons, Inc., Princeton, N.J.

[21] Appl. No.: 444,775

[22] Filed: Nov. 26, 1982

Related U.S. Application Data

[62] Division of Ser. No. 260,659, May 4, 1981, Pat. No. 4,381,297.

[51] Int. Cl.³ .............................. C07F 9/32; C07F 9/58
[52] U.S. Cl. ...................................... 260/941; 546/22; 549/6; 549/218
[58] Field of Search ............. 260/941; 546/22; 549/6, 549/218

[56] References Cited

U.S. PATENT DOCUMENTS

| | | | |
|---|---|---|---|
| 4,105,776 | 8/1978 | Ondetti et al. | 424/274 |
| 4,129,566 | 12/1978 | Ondetti et al. | 546/326 |
| 4,151,172 | 4/1979 | Ondetti et al. | 260/326.2 |
| 4,154,935 | 5/1979 | Ondetti et al. | 546/189 |
| 4,168,267 | 9/1979 | Petrillo | 260/326.2 |
| 4,192,878 | 3/1980 | Ondetti | 424/270 |
| 4,217,359 | 8/1980 | Krapcho | 424/274 |
| 4,234,489 | 11/1980 | Ondetti et al. | 260/326.2 |
| 4,316,896 | 2/1982 | Thorsett et al. | 424/200 |
| 4,316,905 | 2/1982 | Krapcho | 424/274 |
| 4,337,201 | 6/1982 | Petrillo | 548/413 |

FOREIGN PATENT DOCUMENTS

| | | |
|---|---|---|
| 868532 | 10/1978 | Belgium . |
| 2027025 | 2/1980 | United Kingdom . |
| 2028327 | 3/1980 | United Kingdom . |
| 2039478 | 8/1980 | United Kingdom . |

OTHER PUBLICATIONS

Mauger et al., "Analogs and Homologs of Proline and Hydroxyproline" Chem. Review, vol. 66, pp. 47–86 (1966).

*Primary Examiner*—Richard Raymond
*Attorney, Agent, or Firm*—Lawrence S. Levinson; Stephen B. Davis

[57] ABSTRACT

Compounds of the formula

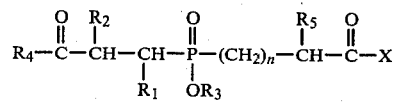

wherein X is an imino acid or ester are disclosed as useful hypotensive agents due to their angiotensin converting enzyme inhibition activity.

6 Claims, No Drawings

SUBSTITUTED CARBONYL PHOSPHINYL-ALKANOYL COMPOUNDS

This is a division of application Ser. No. 260,659 filed May 4, 1981 now U.S. Pat. No. 4,381,297.

BACKGROUND OF THE INVENTION

Petrillo in U.S. Pat. No. 4,168,267 discloses that various phosphinylalkanoyl substituted prolines are useful as hypotensive agents due to their ability to inhibit the angiotensin converting enzyme.

Ondetti et al. in U.S. Pat. No. 4,151,172 discloses that various phosphonoacyl prolines are useful as hypotensive agents due to their ability to inhibit the angiotensin converting enzyme.

Mercaptoacyl derivatives of proline and substituted prolines are known to be useful hypotensive agents due to their angiotensin converting enzyme inhibition activity. Ondetti et al. in U.S. Pat. No. 4,105,776 disclose such compounds wherein the proline ring is unsubstituted or substituted by an alkyl or hydroxy group. Ondetti et al. in U.S. Pat. No. 4,154,935 disclose such compounds wherein the proline ring is substituted with one or more halogens. Ondetti et al. in U.K. patent application No. 2,028,327 disclose such compounds wherein the proline ring is substituted by various ethers and thioethers. Krapcho in U.S. Pat. No. 4,217,359 disclose such compounds wherein the proline ring has a carbamoyloxy substituent. Krapcho in U.K. patent application No. 2,039,478 discloses compounds wherein the proline ring has a diether, dithioether, ketal or thioketal substituent in the 4-position. Krapcho in U.S. Ser. No. 164,985 filed July 1, 1980, now U.S. Pat. No. 4,316,905, discloses such compounds wherein the proline ring has a cycloalkyl, phenyl, or phenyl-lower alkylene substituent. Ondetti et al. in U.S. Pat. No. 4,234,489 disclose such compounds wherein the proline was a keto substituent in the 5-position. Krapcho et al. in U.S. Ser. No. 162,341 filed June 23, 1980, now U.S. Pat. No. 4,310,461, disclose such compounds wherein the proline has an imido, amido, or amino substituent in the 4-position. Iwao et al. in U.K. Pat. application No. 2,027,025 disclose such compounds wherein the proline has an aromatic substituent in the 5-position.

Mercaptoacyl derivatives of 3,4-dehydroproline are disclosed as angiotensin converting enzyme inhibitors by Ondetti in U.S. Pat. No. 4,129,566. Mercaptoacyl derivatives of thiazolidinecarboxylic acid and substituted thiazolidinecarboxylic acid are disclosed as angiotensin converting enzyme inhibitors by Ondetti in U.S. Pat. No. 4,192,878 and by Yoshitomo Pharmaceutical Ind. in Belgian Pat. No. 868,532.

SUMMARY OF THE INVENTION

This invention is directed to new substituted carbonyl phosphinylalkanoyl compounds of formula I and salts thereof $$R_4-\overset{O}{\underset{}{C}}-CH-\overset{R_2}{\underset{R_1}{CH}}-\overset{O}{\underset{OR_3}{P}}-(CH_2)_n-\overset{R_5}{\underset{}{CH}}-\overset{O}{\underset{}{C}}-X. \quad (I)$$

X is an imino acid of the formula

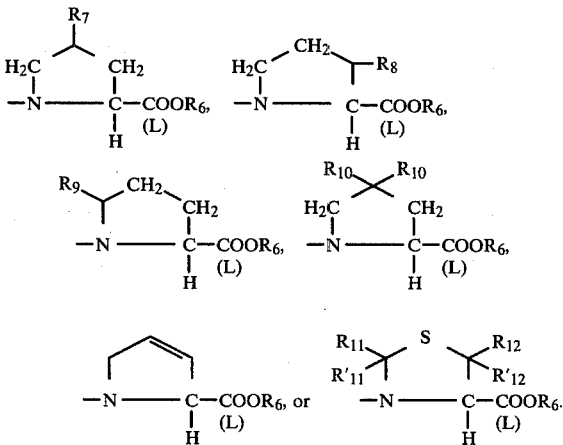

$R_7$ is hydrogen, lower alkyl, halogen, keto, hydroxy,

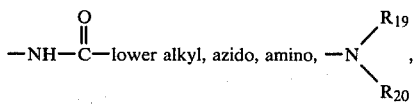

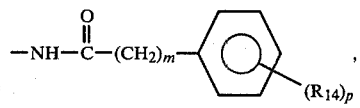

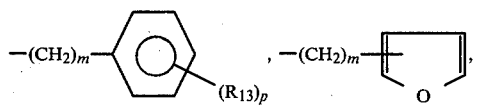

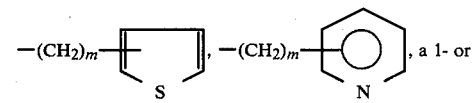

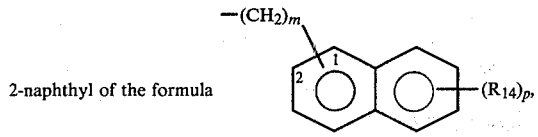

2-naphthyl of the formula

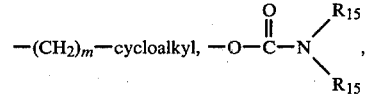

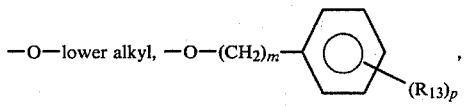

a 1- or 2-naphthyloxy of the formula

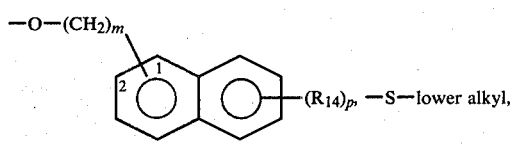

-continued

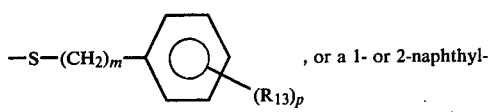, or a 1- or 2-naphthylthio of the formula 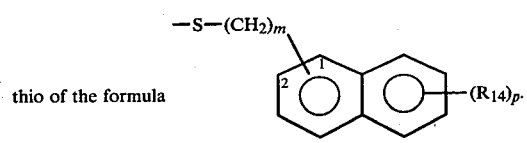

$R_8$ is keto, halogen, 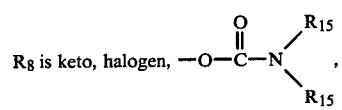,

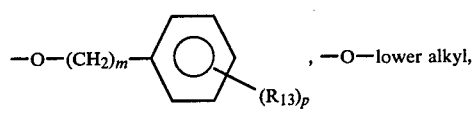, —O—lower alkyl, a 1- or 2-naphthyloxy of the formula

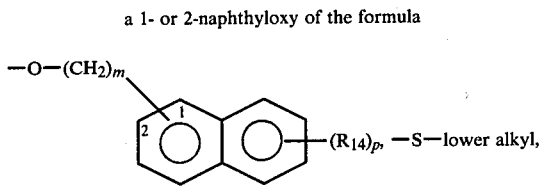, —S—lower alkyl,

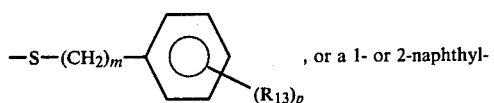, or a 1- or 2-naphthylthio of the formula 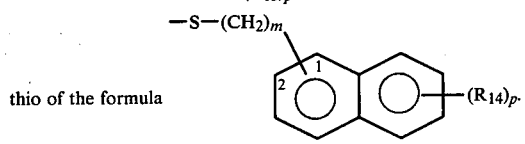

$R_9$ is keto or 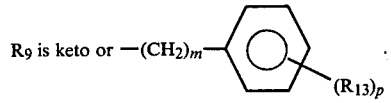

$R_{10}$ is halogen or —Y—$R_{16}$.

$R_{11}$, $R_{11}'$, $R_{12}$ and $R_{12}'$ are independently selected from hydrogen and lower alkyl or $R_{11}'$, $R_{12}$ and $R_{12}'$ are hydrogen and $R_{11}$ is

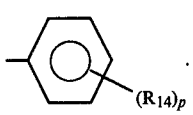

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two or three.

p is one, two or three provided that p is more than one only if $R_{13}$ or $R_{14}$ is hydrogen, methyl, methoxy, chloro, or fluoro.

$R_{15}$ is hydrogen or lower alkyl of 1 to 4 carbons.
Y is oxygen or sulfur.
$R_{16}$ is lower alkyl of 1 to 4 carbons,

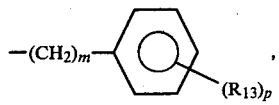, or the $R_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

n is zero or one.

$R_5$ is hydrogen, lower alkyl, halo substituted lower alkyl, benzyl or phenethyl.

$R_3$ and $R_6$ are independently selected from hydrogen, lower alkyl, benzyl, benzhydryl, or $$-\underset{R_{17}}{\underset{|}{CH}}-O-\overset{O}{\underset{\|}{C}}-R_{18}$$

wherein $R_{17}$ is
hydrogen, lower alkyl, or phenyl, and $R_{18}$ is hydrogen, lower alkyl, lower alkoxy, phenyl, or $R_{17}$ and $R_{18}$ taken together are

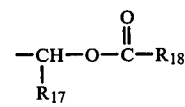

$R_4$ is hydrogen, lower alkyl, halo substituted lower alkyl,

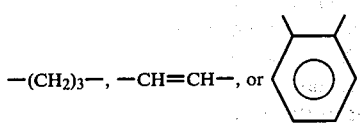

wherein $R_{13}$ and p are as defined above and q is zero or an integer from 1 to 7, cycloalkyl,

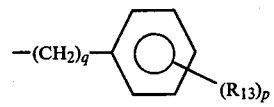

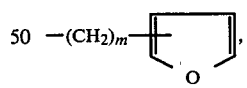

$R_{19}$ is lower alkyl, benzyl, or phenethyl.
$R_{20}$ is hydrogen, lower alkyl, benzyl or phenethyl.
$R_1$ and $R_2$ are independently selected from hydrogen, lower alkyl, halo substituted lower alkyl,

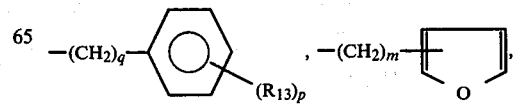

-continued

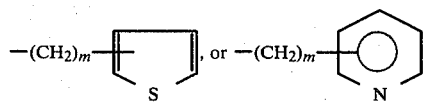

wherein q, $R_{13}$, p and m are as defined above.

DETAILED DESCRIPTION OF THE INVENTION

This invention in its broadest aspects relates to the substituted carbonyl phosphinylalkanoyl compounds of formula I above, to compositions containing such compounds and to the method of using such compounds as anti-hypertensive agents, and to intermediates useful in preparing such compounds.

The term lower alkyl used in defining various symbols refers to straight or branched chain hydrocarbon radicals having up to seven carbons, for example, methyl, ethyl, propyl, isopropyl, butyl, isobutyl, t-butyl, pentyl, isopentyl, etc. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The symbols

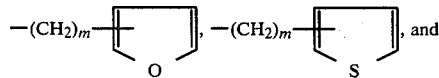

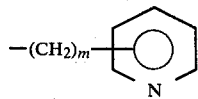

represent that the alkylene bridge is attached to an available carbon atom.

The compounds of formula I are prepared according to the following procedures. An acid or its activated form of formula II wherein $R_3$ is hydrogen, lower alkyl, benzyl, or benzhydryl

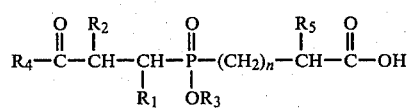 (II)

is coupled with an imino acid or ester of the formula

HX.  (III)

The term activated form refers to the conversion of the acid to a mixed anhydride, symmetrical anhydride, acid chloride, or activated ester, see Methoden der Organischen Chemie (houben-Weyl), Vol. XV, part II, page 1 et seq. (1974) for a review of the methods of acylation. Preferably, the reaction is performed in the presence of a coupling agent such as 1,1-carbonyldiimidazole, or dicyclohexylcarbodiimide.

The products of formula I wherein either or both of $R_3$ and $R_6$ are lower alkyl, benzyl, or benzhydryl can be hydrogenated, for example, by treating with hydrogen in the presence of a palladium on carbon catalyst or chemically treated such as with hydrogen bromide and acetic acid or with trifluoroacetic acid and anisole to yield the products of formula I wherein $R_3$ and $R_6$ are hydrogen.

The ester products of formula I wherein $R_6$ is

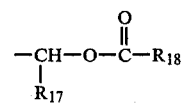

may be obtained by employing the imino acid of formula III in the coupling reaction with the ester grop already in place. Such ester starting materials can be prepared by treating the imino acid with an acid chloride such as

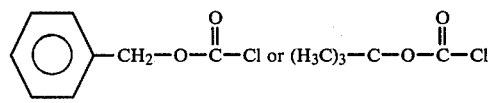

so as to protect the N-atom. The protected imino acid is then reacted in the presence of base with a compound of the formula

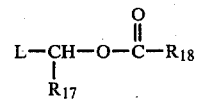

wherein L is a leaving group such as chlorine, bromine, tolylsulfonyl, etc., followed by removal of the N-protecting group such as by treatment with acid or hydrogenation.

The ester products of formula I wherein $R_6$ is

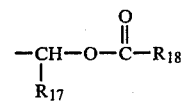

can also be obtained by treating the product of formula I wherein $R_6$ is hydrogen with a molar equivalent of the compound of formula IV. The diester products wherein $R_3$ and $R_6$ are the same and are

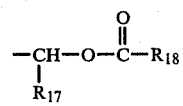

can be obtained by treating the product of formula I wherein $R_3$ and $R_6$ are both hydrogen with two or more equivalents of the compound of formula IV.

The ester products of formula I wherein $R_3$ is

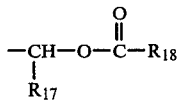

can be obtained by treating the product of formula I wherein $R_3$ is hydrogen and $R_6$ is t-butyl, benzyl or benzhydryl with the compound of formula IV in the presence of base. Removal of the $R_6$ ester group such as by hydrogenation yields the products of formula I wherein $R_3$ is

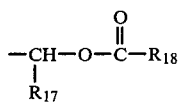

and $R_6$ is hydrogen.

The products of formula I wherein $R_7$ is amino may be obtained by reducing the corresponding products of formula I wherein $R_7$ is azido.

The carboxylic acids of formula II can be prepared by reacting the substituted carbonyl compound of the formula

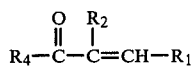

with the dichlorophosphine

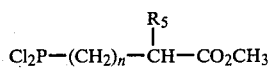

in the presence of acetic anhydride and the alcohol $R_3$—OH or water followed by a reagent such as diazomethane, 1-benzyl-3-p-tolyltriazine, etc., to yield the intermediate

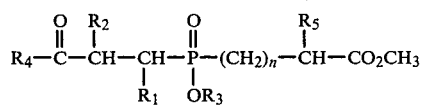

wherein $R_3$ is lower alkyl, benzyl, phenethyl, or benzhydryl. Hydrolysis such as by treatment with hydrochloric acid yields the desired acid of formula II.

The acid of formula II wherein $R_3$ is hydrogen can be obtained by employing water rather than an alcohol in the above procedure or by removal of the $R_3$ ester group from the intermediates of formula VII. Of course, the products of formula I wherein $R_3$ is hydrogen can also be obtained by removal of the ester group after the coupling reaction has been completed.

The various imino acids and esters of formula III are described in the literature and in the various patents and pending U.S. application referred to above. Various substituted prolines are disclosed by Mauger et al., Chem. Review, Vol. 66, p. 47–86 (1966). When the imino acid is known it can be readily converted to the ester by conventional means. For example, the esters where $R_6$ is t-butyl can be obtained by treating the corresponding N-carbobenzyloxyimino acid with isobutylene under acidic conditions and then removing the N-carbobenzyloxy protecting group by catalytic hydrogenation and the esters wherein $R_6$ is benzyl can be obtained by treating the imino acid with benzyl alcohol and thionyl chloride.

As disclosed by Krapcho in U.S. Ser. No. 164,985, now U.S. Pat. No. 4,316,905, the substituted prolines wherein $R_7$ is

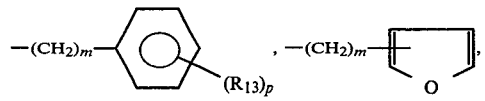

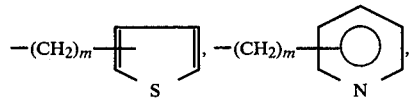

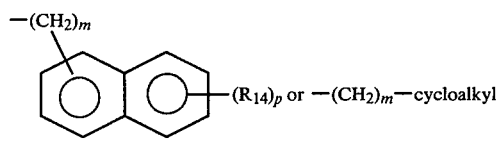

are prepared by reacting a 4-keto proline of the formula

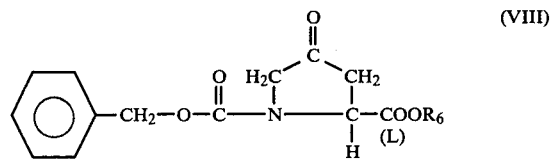

with a solution of the Grignard or lithium reagent

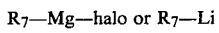

wherein $R_7$ is as defined above and halo is Br or Cl to yield

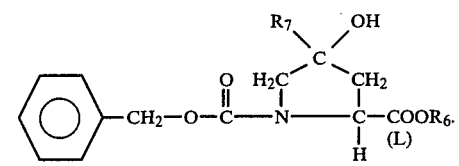

This compound is treated with a dehydrating agent such as p-toluenesulfonic acid, sulfuric acid, potassium bisulfate, or trifluoroacetic acid to yield the 3,4-dehydro-4-substituted proline of the formula

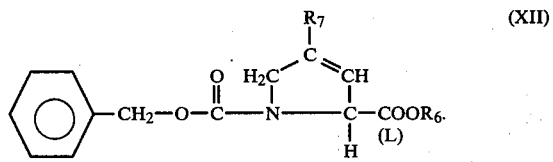

Removal of the N-benzyloxycarbonyl protecting group and hydrogenation of the compound of formula XII yields the desired starting materials. The substituted proline wherein $R_7$ is cyclohexyl can be prepared by further hydrogenation of the 4-phenyl proline compound.

The substituted prolines wherein $R_7$ is the substituted amino group

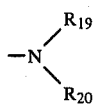

may be prepared by reacting a 4-keto proline of formula (VIII) with the amine

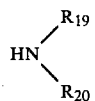

in the presence of hydrogen and catalyst or in the presence of sodium cyanotrihydridoborate.

Preferred compounds of this invention with respect to the imino acid or ester part of the structure of formula I are those wherein:

$R_6$ is hydrogen or

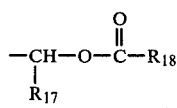

wherein $R_{17}$ is hydrogen or methyl and $R_{18}$ is straight or branched chain lower alkyl of 1 to 4 carbons or phenyl.

$R_7$ is hydrogen.

$R_7$ is hydroxy.

$R_7$ is chloro or fluoro.

$R_7$ is lower alkyl of 1 to 4 carbons or cyclohexyl.

$R_7$ is amino.

$R_7$ is —O—lower alkyl wherein lower alkyl is straight or branched chain of 1 to 4 carbons.

$R_7$ is

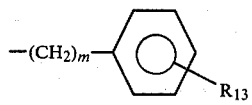

wherein m is zero, one of two, $R_{13}$ is hydrogen, methyl, methoxy, methylthio, chloro, bromo, fluoro, or hydroxy.

$R_7$ is

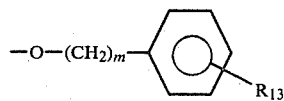

wherein m is zero, one or two, and $R_{13}$ is hydrogen, methyl, methoxy, methylthio, chloro, bromo, fluoro, or hydroxy.

$R_7$ is —S—lower alkyl wherein lower alkyl is straight or branched chain of 1 to 4 carbons.

$R_7$ is

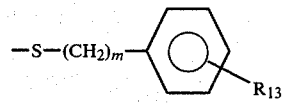

wherein m is zero, one or two, and $R_{13}$ is hydrogen, methyl, methoxy, methylthio, chloro, bromo, fluoro, or hydroxy.

$R_8$ is —O—lower alkyl wherein lower alkyl is straight or branched chain of 1 to 4 carbons.

$R_8$ is

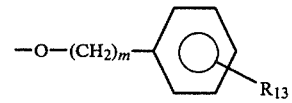

wherein m is zero, one or two, and $R_{13}$ is hydrogen, methyl, methoxy, methylthio, chloro, bromo, fluoro, or hydroxy.

$R_8$ is —S—lower alkyl wherein lower alkyl is straight or branched chain of 1 to 4 carbons.

$R_8$ is

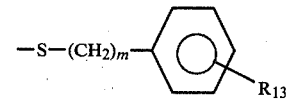

wherein m is zero, one or two, and $R_{13}$ is hydrogen, methyl, methoxy, methylthio, chloro, bromo, fluoro, or hydroxy.

$R_9$ is phenyl, 2-hydroxyphenyl, or 4-hydroxyphenyl.

$R_{10}$ are both fluoro or chloro.

$R_{10}$ are both —Y—$R_{16}$ wherein Y is O or S, $R_{16}$ is straight or branched chain alkyl of 1 to 4 carbons or the $R_{16}$ groups join to complete an unsubstituted 5- or 6-membered ring or said ring in which one or more of the carbons has a methyl or dimethyl substiutent.

$R_{11}$, $R_{11}'$, $R_{12}$ and $R_{12}'$ are all hydrogen, or $R_{11}$ is phenyl, 2-hydroxyphenyl or 4-hydroxyphenyl and $R_{11}'$, $R_{12}$ and $R_{12}'$ are hydrogen.

Most preferred compounds of this invention with respect to the imino acid or ester part of the structure of formula I are those wherein: X is:

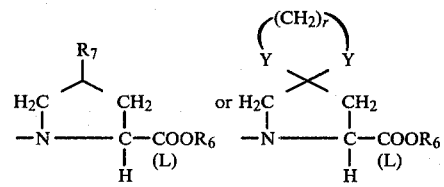

$R_6$ is hydrogen or

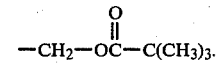

$R_7$ is hydrogen.

$R_7$ is cyclohexyl.

$R_7$ is lower alkoxy of 1 to 4 carbons.

$R_7$ is

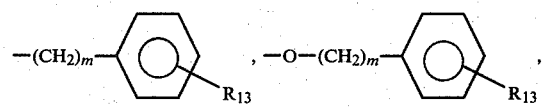

-continued

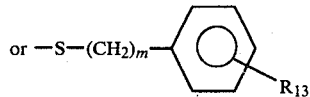

wherein m is zero, one, or two and $R_{13}$ is hydrogen, methyl, methoxy, methylthio, Cl, Br, F or hydroxy.

Y is oxygen or sulfur and r is two or three, especially wherein Y is sulfur and r is two.

Preferred compounds of this invention with respect to the phosphinylalkanoyl sidechain of the structure of formula I are those wherein:

$R_3$ is hydrogen or

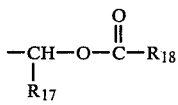

wherein $R_{17}$ is hydrogen or methyl and $R_{18}$ is straight or branched chain lower alkyl of 1 to 4 carbons or phenyl, especially hydrogen or

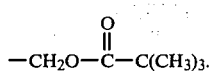

$R_4$ is lower alkyl of 1 to 7 carbons; $CF_3$;

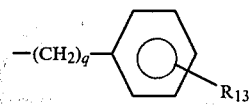

wherein q is zero or an integer from 1 to 4 and $R_{13}$ is hydrogen, methyl, methoxy, methylthio, chloro, bromo, fluoro, or hydroxy; cycloalkyl of 5 or 6 carbons;

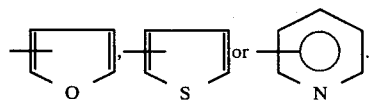

$R_5$ is hydrogen.
n is zero.
$R_2$ is hydrogen.
$R_1$ is lower alkyl of 1 to 7 carbons or

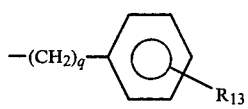

wheren q is zero or an integer from 1 to 4 and $R_{13}$ is hydrogen, methyl, methoxy, methylthio, chloro, bromo, fluoro or hydroxy; especially

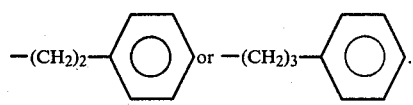

The compounds of this invention wherein at least one of $R_3$ or $R_6$ is hydrogen, form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product. The salts are formed using conventional techniques.

As shown above, the imino acid or ester portion of the molecule of the products of formula I is in the L-configuration. Depending upon the definitions of $R_1$, $R_2$ and $R_5$ one or more asymmetric centers may be present in the phosphinylalkanoyl sidechain. Thus, some of the compounds can accordingly exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_7$, $R_8$ and $R_9$ substituent in the starting material of formula III.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(resin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg. per kilogram of body weight per day is appropriate to reduce blood pressure. The substance is preferably administered orally, but parenteral routes such as the subcutaneous, intramuscular, intravenous or intraperitoneal route can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade.

EXAMPLE 1

(±)-1-[[Hydroxy[3-oxo-3-phenyl-1-(2-phenylethyl)-propyl]phosphinyl]acetyl]-L-proline, dilithium salt

(a) Carbomethoxymethyldichlorophosphine

Ketene is passed through a solution of tributyltin methoxide (64 g., 0.199 mole) in 200 ml. of anhydrous ether at 0° until Tlc (silica gel, methanol:dichloromethane; 1:9) indicates complete consumption of starting material ($R_f$ equals 0.14). The ether is removed in vacuo and the residue distilled to give 62.75 g. of carbomethoxymethyl tributyltin as a pale yellow liquid; b.p. 117°-120° (0.8 mm Hg.).

A mixture of carbomethoxymethyl tributyltin (80 g., 0.22 mole) and phosphorous trichloride (80 ml., 0.92 mole) is treated with 2,2'-azobisisobutyronitrile (230 mg., 1.4 mmole) and slowly heated to reflux under argon. After refluxing for 30 minutes, the excess phosphorous trichloride is distilled off under reduced pressure. Distillation of the residue gives 19.4 g. of carbomethoxymethyldichlorophosphine as a colorless liquid; b.p. 52° (2 mm of Hg).

(b) 1,5-Diphenyl-2-penten-1-one

A mixture of 3-phenylpropionaldehyde (1.8 g., 13.43 mmole), phenacyltriphenyl-phosphonium bromide (6.25 g., 13.56 mmole), sodium carbonate (1.6 g., 15.09 mmole) and water (14 ml.) in tetrahydrofuran (46 ml.) is refluxed for 18.5 hours under an atmosphere of argon. The cooled mixture is diluted with ethyl ether, the layers separate, and the organic phase is washed with saturated sodium chloride and dried over MgSO₄—Na₂SO₄. The solvent is evaporated, the residue is triturated with hot hexane and insoluble triphenyl phosphine oxide is filtered off. The residue obtained on evaporation of the hexane is purified by flash chromatography on silica gel (50 g.) eluting with ethyl ether/hexane (1:6) to give 2.7 g. of 1,5-diphenyl-2-penten-1-one as a pale yellow oil. Tlc, ethyl ether/hexane (1:2) $R_f$ at 0.65.

(c) [Ethoxy[3-oxo-3-phenyl-1-(2-phenylethyl)-propyl]phosphinyl]acetic acid, methyl ester A mixture of 1,5-diphenyl-2-penten-1-one (1.013 g., 4.29 mmole) and carbomethoxymethyldichlorophosphine (1.52 g., 8.7 mmole) in acetic anhydride (2 ml.) is stirred at 60° (bath temperature) for 19 hours in an argon atmosphere. The volatiles are removed in vacuo (0.5 mm. Hg, 60°), the residue is taken up in absolute ethanol (5 ml.) and refluxed for 45 minutes. After evaporation of the ethanol, the resulting residue is purified by flash chromatography on silica gel (100 g.) eluting with ethyl ether/dichloromethane (1:9) to give 1.35 g. of [ethoxy[3-oxo-3-phenyl-1-(2-phenylethyl)propyl]phosphinyl]acetic acid, methyl ester as a pale yellow oil, $R_f$(ethyl ether/dichloromethane; 1:1) 0.53.

(d) [Ethoxy[3-oxo-3-phenyl-1-(2-phenylethyl)-propyl]phosphinyl]acetic acid

A solution of the product from part (c) (1.345 g., 3.35 mmole) in glacial acetic acid (10 ml.) is treated with concentrated hydrochloric acid (5 ml.) and stirred at room temperature for 46 hours. The mixture is poured onto an ice-water mixture and extracted with ethyl acetate. The ethyl acetate extract is washed with water and then extracted with saturated sodium bicarbonate solution. The ethyl acetate phase is dried over Na₂SO₄ and evaporated to give 210 mg. of recovered starting material. The sodium bicarbonate extracts are acidified with concentrated hydrochloric acid and extracted with ethyl acetate. The ethyl acetate extract is washed with saturated sodium chloride, dried over Na₂SO₄ and evaporated. The residue is purified by flash chromatography on silica gel (70 g.) eluting with acetic acid/methanol/dichloromethane (0.5:4.5:95.0) to give 834 mg. of [ethoxy[3-oxo-3-phenyl-1-(2-phenylethyl)propyl]phosphinyl]acetic acid as a colorless glass, $R_f$ (acetic acid/methanol/dichloromethane 1:1:18) 0.38.

(e) (±)-1-[[Ethoxy[3-oxo-3-phenyl-1-(2-phenylethyl)-propyl]phosphinyl]acetyl]-L-proline, phenylmethyl ester A solution of the product from part (d) (834 mg., 2.15 mmole) in dry acetonitrile (8 ml.) is treated with N,N'-carbonyldiimidazole (375 mg., 2.31 mmole) and stirred at 0° (ice bath) under argon for 1.5 hours. The resulting solution is then treated with L-proline, benzyl ester (455 mg., 2.22 mmole) in acetonitrile and stirred at room temperature for 4 hours. The mixture is evaporated to dryness and the residue is taken up in ethyl acetate. The ethyl acetate solution is washed successively with 5% potassium bisulfate, saturated sodium bicarbonate and saturated sodium chloride, dried over Na₂SO₄ and evaporated. The residue (1.325 g.) is purified by flash chromatography on silica gel (75 g.) eluting with 1% methanol/dichloromethane to give (±)-1-[[ethoxy[3-oxo-3-phenyl-1-(2-phenylethyl)propyl]phosphinyl]acetyl]-L-proline, phenylmethyl ester (74%) as a colorless glass, $R_f$(methanol/dichloromethane; 5:95) 0.29.

(f) (±)-1-[[Hydroxy[3-oxo-3-phenyl-1-(2-phenylethyl)-propyl]phosphenyl]acetyl]-L-proline, phenylmethyl ester A solution of the product from part (e) (1.146 g., 1.99 mmole) in dry dichloromethane (6 ml.) is treated with bromotrimethylsilane (0.55 ml., 4.17 mmole) and stirred at room temperature under argon. After 3 hours, additional bromotrimethylsilane (0.2 ml.) is added and stirring continued for 1 hour. The excess bromotrimethylsilane and dichloromethane are removed in vacuo and the residue is treated with water and ethyl acetate and stirred for 15 minutes. The aqueous phase is separated and the ethyl acetate layer is washed with saturated sodium chloride, dried over Na$_2$SO$_4$ and evaporated to give (±)-1-[[hydroxy[3-oxo-3-phenyl-1-(2-phenylethyl)propyl]phosphinyl]acetyl]-L-proline, phenylmethyl ester (100%) as a white foam, R$_f$ (acetic acid/methanol/dichloromethane 1:1:18) 0.42.

(g)
(±)-1-[[Hydroxy[3-oxo-3-phenyl-1-(2-phenylethyl)propyl]phosphinyl]acetyl]-L-proline A solution of the product from part (f) (1.085 g., 1.98 mmole) in glacial acetic acid (10 ml.) is treated with 7.2 N hydrogen bromide/acetic acid (10 ml.) and stirred at room temperature for 26 hours. The mixture is poured onto ice and thoroughly extracted with ethyl acetate. The combined ethyl acetate extracts are washed with saturated sodium chloride solution, dried over Na$_2$SO$_4$ and evaporated. The residue is taken up in 1 N lithium hydroxide (4 ml.), diluted with water and extracted with ethyl ether. The aqueous phase is acidified with concentrated hydrochloric acid and extracted with ethyl acetate. The ethyl acetate extract is washed with saturated sodium chloride solution, dried over Na$_2$SO$_4$ and evaporated to give 857 mg. of (±)-1-[[hydroxy[3-oxo-3-phenyl-1-(2-phenylethyl)propyl]phosphinyl]acetyl]-L-proline (94.5%) as a colorless foam, R$_f$ (acetic acid/methanol/dichloromethane 1:1:8) 0.69.

(h)
(±)-1-[[Hydroxy[3-oxo-3-phenyl-1-(2-phenylethyl)propyl]phosphinyl]acetyl]-L-proline, dilithium salt The product from part (g) (857 mg., 1.875 mole) is taken up in 1 N lithium hydroxide (2 ml., 2.0 mmole) and passed slowly through a column of AG-50W-X8 (Li$^+$ form, 30 ml. settled volume). The eluate is lyophilized to give 770 mg. of (±)-1-[[hydroxy[3-oxo-3-phenyl-1-(2-phenylethyl)propyl]phosphinyl]acetyl]-L-proline, dilithium salt as a colorless lyophilizate.

Anal. calc'd. for C$_{24}$H$_{26}$Li$_2$NO$_6$P·1.5 H$_2$O: C, 58.08; H, 5.89; N, 2.82; P, 6.24
Found: C, 57.84; H, 5.82; N, 2.79; P, 6.20.

EXAMPLE 2

(±)-1-[[Hydroxy[1-(2-oxo-2-phenylethyl)heptyl]phosphinyl]acetyl]-L-proline, dilithium salt (a) 1-Phenyl-2-nonen-1-one A mixture of heptaldehyde (3.4 g., 29.8 mmole), phenacyltriphenylphosphonium bromide (13.8 g., 30.0 mmole), sodium carbonate (3.5 g., 33 mmole) and water (30 ml.) in tetrahydrofuran (100 ml.) is refluxed for 22 hours under an atmosphere of argon. The cooled mixture is diluted with ethyl ether, the layers are separated, and the organic phase is washed with saturated sodium chloride and dried over MgSO$_4$/Na$_2$SO$_4$. The solvent is evaporated, the residue is triturated with hot hexane and insoluble triphenyl phosphine oxide is filtered off. The residue obtained on evaporation of the hot hexane is purified by flash chromatography on silica gel (110 g.) eluting with ethyl ether/hexane (1:20) to give 5.7 g. of 1-phenyl-2-nonen-1-one as a pale yellow oil, R$_f$ (ethyl ether/hexane 1:4) 0.67.

(b)
[Ethoxy[1-(2-oxo-2-phenylethyl)heptyl]phosphinyl]acetic acid, methyl ester

A mixture of the product from part (a) (2.15 g., 10 mmole) and carbomethoxymethyldichlorophosphine (3.05 g., 17.4 mmole) in acetic anhydride (4 ml.) is stirred at 70° (bath temperature) for 22 hours in an argon atmosphere. The volatiles are removed in vacuo (0.5 mm Hg.; 60°), the residue is taken up in absolute ethanol (10 ml.) and refluxed for 45 minutes. After evaporation of the ethanol, the resulting residue is purified by flash chromatography on silica gel (110 g.) eluting with ethyl ether/dichloromethane (1:9) to give 3.2 g. of [ethoxy[1-(2-oxo-2-phenylethyl)heptyl]phosphinyl]acetic acid, methyl ester as a pale yellow oil, R$_f$ (ethyl ether/dichloromethane 1:1) 0.57.

(c)
[Ethoxy[1-(2-oxo-2-phenylethyl)heptyl]phosphinyl]acetic acid

A solution of the product from part (b) (3.10 g., 8.115 mmole) in glacial acetic acid (10 ml.) is treated with concentrated hydrochloric acid (5 ml.) and stirred at room temperature for 46 hours. The mixture is poured onto an ice-water mixture and extracted with ethyl acetate. The ethyl acetate extract is washed with water, saturated sodium chloride solution, dried over Na$_2$SO$_4$ and evaporated. The residue is purified by flash chromatography on silica gel (85 g.) eluting with acetic acid/methanol/dichloromethane (0.5:3.0:100) to give 470 mg. of recovered starting material and 2.0 g. of [ethoxy[1-(2-oxo-2-phenylethyl)heptyl]phosphinyl]acetic acid as a colorless glass, R$_f$ (acetic acid/methanol/dichloromethane 0.5:5:100) 0.32.

(d)
(±)-1-[[Ethoxy[1-(2-oxo-2-phenylethyl)-heptyl]phosphinyl]acetyl]-L-proline, phenylmethyl ester A solution of the product from part (c) (1.95 g., 5.299 mmole) in dry acetonitrile (20 ml.) is treated with N,N'-carbonyldiimidazole (850 mg., 5.247 mmole) and stirred at 0° (ice bath) under argon for 1.5 hours. The resulting solution is then treated with L-proline, benzyl ester (1.12 g., 5.46 mmole) in acetonitrile and stirred at room temperature for 18 hours. The mixture is evaporated to dryness and the residue is taken up in ethyl acetate. The ethyl acetate solution is washed successively with 5% potassium bisulfate, saturated sodium bicarbonate and saturated sodium chloride and evaporated. The residue is purified by flash chromatography on silica gel (75 g.) eluting with 2% methanol/dichloromethane to give 2.80 g. of (±)-1-[[ethoxy[1-(2-oxo-2-phenylethyl)heptyl]phosphinyl]acetyl]-L-proline, phenylmethyl ester as a colorless glass, R$_f$ (methanol/dichloromethane 5:95) 0.43.

(e)
(±)-1-[[Hydroxy[1-(2-oxo-2-phenylethyl)-heptyl]phosphinyl]acetyl]-L-proline, phenylmethyl ester A solution of the product from part (d) (2.75 g., 4.95 mmole) in dry dichloromethane (15 ml.) is treated with bromotrimethylsilane (1.8 ml., 13.6 mmole) and stirred at room temperature under argon. After 3.5 hours, the excess bromotrimethylsilane and dichloromethane are removed in vacuo, the residue is treated with water and ethyl acetate and stirred for 15 minutes. The aqueous phase is separated and the ethyl acetate layer is washed with saturated sodium chloride, dried over Na$_2$SO$_4$ and evaporated to give 2.60 g. of (±)-1-[[hydroxy[1-(2-oxo-2-phenylethyl)heptyl]phosphinyl]acetyl]-L-proline, phenylmethyl ester as a colorless glass R$_f$ (acetic acid/methanol/dichloromethane 1:1:18) 0.61.

(f)
(±)-1-[[Hydroxy[1-(2-oxo-2-phenylethyl)-heptyl]phosphinyl]acetyl]-L-proline

A solution of the product from part (e) (2.55 g., 4.84 mmole) in glacial acetic acid (15 ml.) is treated with 7.2 N hydrogen bromide/acetic acid (15 ml.) and stirred at room temperature for 22 hours. The mixture is poured onto ice and thoroughly extracted with ethyl acetate. The combined ethyl acetate extracts are washed with saturated sodium chloride, dried over $Na_2SO_4$ and evaporated. The residue is taken up in 1 N lithium hydroxide (10 ml.), diluted with water and extracted with ethyl ether. The aqueous phase is acidified with concentrated hydrochloric acid and extracted with ethyl acetate. The ethyl acetate extract is washed with saturated sodium chloride solution, dried over $Na_2SO_4$ and evaporated to give 2.0 g. of (±)-1-[[hydroxy[1-(2-oxo-2-phenylethyl)heptyl]phosphinyl]acetyl]-L-proline as a colorless foam, $R_f$ (acetic acid/methanol/dichloromethane 1:1:8) 0.35.

(g)
(±)-1-[[Hydroxy[1-(2-oxo-2-phenylethyl)heptyl]phosphinyl]acetyl]-L-proline, dilithium salt The product from part (f) (2.0 g., 4.58 mmole) is taken up in 1 N lithium hydroxide (5 ml., 5.0 mmole) and passed slowly through a column of AG-50W-X8 ($Li^+$, 60 ml. settled volume). The eluate is lyophilized to give 1.9 g. of (±)-1-[[hydroxy[1-(2-oxo-2-phenylethyl)heptyl]-phosphinyl]acetyl]-L-proline, dilithium salt as a colorless lyophilizate.

Anal. calc'd. for $C_{22}H_{30}Li_2NO_6P \cdot 0.5\ H_2O$: C, 57.65; H, 6.82; N, 3.07; P, 6.76
Found: C, 57.51; H, 7.13; N, 3.03; P, 6.77.

EXAMPLE 3
(±)-1-[[Hydroxy[3-oxo-1-(2-phenylethyl)octyl]-phosphinyl]acetyl]-L-proline, dilithium salt (a) 1-Phenyl-3-decen-5-one A mixture of 3-phenylpropanol (2.68 g., 20 mmole), triphenyl-(2-keto-n-heptyl)phosphonium chloride (8.22 g., 20 mmole), sodium carbonate (2.36 g., 22.3 mmole) and water (20 ml.) in tetrahydrofuran (70 ml.) is refluxed for 6 hours under an atmosphere of argon. The cooled mixture is diluted with ethyl ether and the layer separate. The organic phase is washed with saturated sodium chloride solution, dried over $Na_2SO_4$ and evaporated. The residue is taken up in hexane and insoluble triphenyl phosphine oxide is filtered off. The residue obtained on evaporation of the hexane is purified by flash chromatography on silica gel (120 g.) eluting with ethyl ether/hexane (1:30) to give two isomers of 1-phenyl-3-decen-5-one; 2.93 g. $R_f$ (ethyl ether/hexane 1:4) 0.73 and 0.42 g. $R_f$ (ethyl ether/hexane 1:4) 0.85.

(b)
[Ethoxy[3-oxo-1-(2-phenylethyl)octyl]phosphinyl]acetic acid, methyl ester

A mixture of 1-phenyl-3-decen-5-one from part (a) (3.5 g., 15.22 mmole) and carbomethoxymethyldichlorophosphine (4.85 g., 27.7 mmole) in acetic anhydride (6 ml.) is stirred at 60° (bath temperature) for 24 hours in an argon atmosphere. The volatiles are removed in vacuo (0.5 mm Hg., 60°), the residue is taken up in absolute ethanol (10 ml.) and refluxed for 1.5 hours. After evaporation of the ethanol, the resulting residue is purified by flash chromatography on silica gel (110 g.) eluting with ethyl ether/dichloromethane (1:9) to give 1.5 g. of [ethoxy[3-oxo-1-(2-phenylethyl)octyl]-phosphinyl]acetic acid, methyl ester as a pale yellow oil, $R_f$ (ethyl ether/dichloromethane 1:1) 0.45.

(c)
[Ethoxy[3-oxo-1-(2-phenylethyl)octyl]phosphinyl]acetic acid

A solution of the product from part (b) (1.5 g., 3.79 mmole) in glacial acetic acid (5 ml.) is treated with concentrated hydrochloric acid (2.5 ml.) and stirred at room temperature for 46 hours. The mixture is poured onto an ice-water mixture and extracted with ethyl acetate. The ethyl acetate extract is washed with water, saturated sodium chloride solution, dried over $Na_2SO_4$ and evaporated. The residue is purified by flash chromatography on silica gel (75 g.) eluting with acetic acid/methanol/dichloromethane (0.5:2.0:100) to give 130 mg. of recovered starting material and 1.2 g. of [ethoxy[3-oxo-1-(2-phenylethyl)octyl]phosphinyl]acetic acid as a colorless glass, $R_f$ (acetic acid/methanol/dichloromethane 0.5:5:100) 0.32.

(d)
(±)-1-[[Ethoxy[3-oxo-1-(2-phenylethyl)-octyl]phosphinyl]acetyl]-L-proline, phenylmethyl ester A solution of the product from part (c) (1.18 g., 3.09 mmole) in dry acetonitrile (15 ml.) is treated with N,N'-carbonyldiimidazole (500 mg., 3.09 mmole) and stirred at 0° (ice bath) under an argon atmosphere for 1.5 hours. The resulting solution is then treated with L-proline, benzyl ester (660 mg., 3.22 mmole) in acetonitrile and stirred at room temperature for 6 hours. The mixture is evaporated to dryness and the residue is taken up in ethyl acetate. The ethyl acetate solution is washed successively with 5% potassium bisulfate, saturated sodium bicarbonate and saturated sodium chloride, dried over $Na_2SO_4$ and evaporated. The residue is purified by flash chromatography on silica gel (75 g.) eluting with 2% methanol/dichloromethane to give 1.47 g. of (±)-1-[[ethoxy[3-oxo-1-(2-phenylethyl)octyl]phosphinyl]acetyl]-L-proline, phenylmethyl ester as a colorless glass, $R_f$ (methanol/dichloromethane 5:95) 0.47.

(e)
(±)-1-[[Hydroxy[3-oxo-1-(2-phenylethyl)octyl]phosphinyl]acetyl]-L-proline, phenylmethyl ester A solution of the product from part (d) (1.42 g., 2.5 mmole) in dry dichloromethane (5 ml.) is treated with bromotrimethylsilane (0.9 ml., 6.82 mmole) and stirred at room temperature under argon. After 17 hours, the excess bromotrimethylsilane and dichloromethane are removed in vacuo, the residue is treated with water and ethyl acetate and stirred for 10 minutes. The aqueous phase is separated and the ethyl acetate layer is washed with saturated sodium chloride, dried over $Na_2SO_4$ and evaporated to give 1.34 g. (±)-1-[[hydroxy[3-oxo-1-(2-phenylethyl)octyl]phosphinyl]acetyl]-L-proline, phenylmethyl ester as a colorless glass, $R_f$ (acetic acid/methanol/dichloromethane 1:1:18) 0.59.

(f)
(±)-1-[[Hydroxy[3-oxo-1-(2-phenylethyl)-octyl]phosphinyl]acetyl]-L-proline

A solution of the product from part (e) (1.29 g., 2.38 mmole) in glacial acetic acid (8 ml.) is treated with 7.2 N hydrogen bromide/acetic acid (8 ml.) and stirred at room temperature for 18 hours. The mixture is poured onto ice and thoroughly extracted with ethyl acetate. The combined ethyl acetate extracts are washed with saturated sodium chloride solution, dried over $Na_2SO_4$ and evaporated. The residue is taken up in 1 N lithium hydroxide (5 ml.), diluted with water and extracted with ethyl ether. The aqueous phase is acidified with concentrated hydrochloric acid and extracted with ethyl acetate. The ethyl acetate extract is washed with saturated sodium chloride solution, dried over $Na_2SO_4$ and evaporated to give 1.05 g. of (±)-1-[[hydroxy[3-oxo-1-(2-phenylethyl)octyl]phosphinyl]acetyl]-L-proline as a colorless foam, $R_f$ (acetic acid/methanol/dichloromethane 1:1:8) 0.54.

(g) (±)-1-[[Hydroxy[3-oxo-1-(2-phenylethyl)octyl]phosphinyl]acetyl]-L-proline, dilithium salt The product from part (f) (1.05 g., 2.33 mmole) is taken up in 1 N lithium hydroxide (2.5 ml., 2.5 mmole) and passed slowly through a column of AG-50W-X8 (Li+, 30 ml. settled volume). The eluate is lyophilized to give 1.02 g. of (±)-1-[[hydroxy[3-oxo-1-(2-phenylethyl)octyl]phosphinyl]acetyl]-L-proline, dilithium salt as a colorless lyophilizate.

Anal. calc'd. for $C_{23}H_{32}Li_2NO_6P \cdot H_2O$: C, 57.39; H, 7.12; N, 2.91; P, 6.43

Found: C, 57.39; H, 7.10; N, 3.00; P, 6.20.

EXAMPLES 4–68

Following the procedure of Examples 1 to 3 but coupling the carboxylic acid shown in Col. I with the imino acid ester shown in Col. II one obtains the product shown in Col. III. The $R_3$ and $R_6$ ester groups can be removed to yield the corresponding diacid ($R_3$ and $R_6$ are hydrogen). In the case of Examples 63–68 only the $R_3$ ester group is removed.

| | Col. I $O\ R_2\ \ \ \ \ \ \ \ \ \ \ \ \ \ \ R_5$ $R_4-C-CH-CH-(CH_2)_n-CH-COOH$ $\ \ \ \ \ \ \ \ \ \ R_1\ OR_3$ $\ \ \ \ \ \ \ \ \ \ \ \ \ \ O$ | | | Col. II HX | Col. III $O\ R_2\ \ \ \ \ \ \ \ \ \ \ \ \ \ \ R_5\ O$ $R_4-C-CH-CH-(CH_2)_n-CH-C-X$ $\ \ \ \ \ \ \ \ \ \ R_1\ OR_3$ $\ \ \ \ \ \ \ \ \ \ \ \ \ \ O$ | | |
|---|---|---|---|---|---|---|---|
| Ex. | $R_4$ | $R_1$ | $R_2$ | $R_3$ | n | $R_5$ | X |
| 4 | ![phenyl] | $-(CH_2)_2-C_6H_5$ | —H | —$C_2H_5$ | one | —H | ![piperidine-COOCH2Ph (L)] |
| 5 | ![phenyl] | $-(CH_2)_2-C_6H_5$ | —H | —$CH_2$—$C_6H_5$ | zero | —$CH_3$ | ![4-OH piperidine-COOCH2Ph (L)] |
| 6 | ![phenyl] | $-CH_2-C_6H_5$ | —$CH_3$ | —$C_2H_5$ | zero | —$CH_2CCl_3$ | ![4-CH3 piperidine-COOCH2Ph (L)] |
| 7 | ![thiophene] | $-CH_2-C_6H_5$ | —H | —$C(CH_3)_3$ | zero | —$CH_2$—$C_6H_5$ | ![4-C(CH3)3 piperidine-COOCH2Ph (L)] |
| 8 | ![furan] | $-(CH_2)_2-C_6H_5$ | —H | —$C_2H_5$ | one | —H | ![4-Cl piperidine-COOCH2Ph (L)] |

-continued

| | Col. I $R_4-\overset{O}{\overset{\|}{C}}-CH-\overset{R_2}{\underset{\|}{CH}}-\overset{O}{\underset{\|}{P}}-(CH_2)_n-\overset{R_5}{\underset{\|}{CH}}-COOH$ $\phantom{R_4-\overset{O}{\overset{\|}{C}}-CH-}R_1\phantom{-}OR_3$ | | | | Col. II HX | Col. III $R_4-\overset{O}{\overset{\|}{C}}-CH-\overset{R_2}{\underset{\|}{CH}}-\overset{O}{\underset{\|}{P}}-(CH_2)_n-\overset{R_5}{\underset{\|}{CH}}-\overset{O}{\overset{\|}{C}}-X$ $\phantom{R_4-\overset{O}{\overset{\|}{C}}-CH-}R_1\phantom{-}OR_3$ | | |
|---|---|---|---|---|---|---|---|---|
| Ex. | $R_4$ | $R_1$ | $R_2$ | $R_3$ | n | $R_5$ | X | |
| 9 | 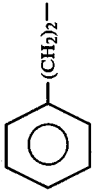 | 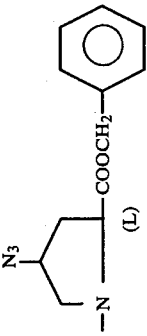 | —H | —$C_2H_5$ | zero | —H | 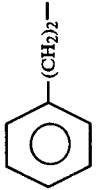 | |
| 10 | 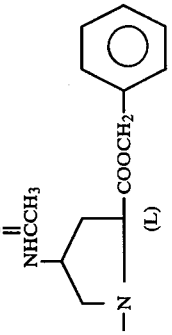 | 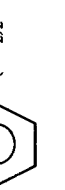 | —H | —$C_2H_5$ | zero | —H | 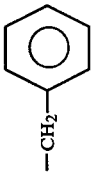 | |
| 11 |  | —H | —H | —$CH_2$—⌬ | zero | —$CH_3$ | 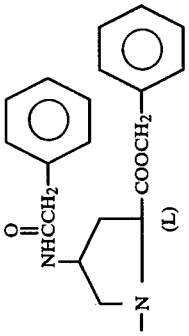 | |
| 12 | ⌬—CH₃ |  | —H | —$C_2H_5$ | one | —H | (see above) | |

-continued

| | Col. I | | | Col. II | Col. III | | |
|---|---|---|---|---|---|---|---|
| | $R_4-\overset{O}{\overset{\|}{C}}-\overset{R_2}{\overset{\|}{CH}}-\overset{}{\overset{}{CH}}-\overset{O}{\overset{\|}{P}}-(CH_2)_n-\overset{R_5}{\overset{\|}{CH}}-COOH$ with $R_1$, $OR_3$ | | | HX | $R_4-\overset{O}{\overset{\|}{C}}-\overset{R_2}{\overset{\|}{CH}}-\overset{}{\overset{}{CH}}-\overset{O}{\overset{\|}{P}}-(CH_2)_n-\overset{R_5}{\overset{\|}{CH}}-\overset{O}{\overset{\|}{C}}-X$ with $R_1$, $OR_3$ | | |
| Ex. | $R_4$ | $R_1$ | $R_2$ | $R_3$ | n | $R_5$ | X |
| 13 | 4-F-C$_6$H$_4$- | -(CH$_2$)$_2$-C$_6$H$_5$ | -H | -C$_2$H$_5$ | zero | -H | -N[CH$_2$CH(C$_6$H$_5$)]CH(COOCH$_2$C$_6$H$_5$)- (L) |
| 14 | C$_6$H$_5$- | -(CH$_2$)$_3$-C$_6$H$_5$ | -H | -C$_2$H$_5$ | zero | -H | -N[CH$_2$CH(C$_6$H$_5$)]CH(COOCH$_2$C$_6$H$_5$)- (L) |
| 15 | 4-H$_3$CO-C$_6$H$_4$- | -(CH$_2$)$_2$-C$_6$H$_5$ | -H | -C$_2$H$_5$ | zero | -H | -N[CH$_2$CH(CH$_2$C$_6$H$_5$)]CH(COOCH$_2$C$_6$H$_5$)- (L) |

-continued

| | Col. I $R_4-\overset{O}{\overset{\|}{C}}-CH-\overset{R_2}{\overset{\|}{CH}}-\overset{O}{\overset{\|}{P}}-(CH_2)_n-\overset{R_5}{\overset{\|}{CH}}-COOH$ $\qquad R_1 \quad OR_3$ | | | | Col. II HX | Col. III $R_4-\overset{O}{\overset{\|}{C}}-CH-\overset{R_2}{\overset{\|}{CH}}-\overset{O}{\overset{\|}{P}}-(CH_2)_n-\overset{R_5}{\overset{\|}{CH}}-\overset{O}{\overset{\|}{C}}-X$ $\qquad R_1 \quad OR_3$ |
|---|---|---|---|---|---|---|---|
| Ex. | $R_4$ | $R_1$ | $R_2$ | $R_3$ | n | $R_5$ | X |
| 16 | H— | 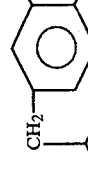 | —H |  | zero | —H |  |
| 17 | 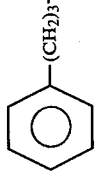 | 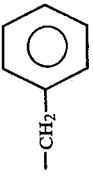 | —H | —$C_2H_5$ | zero | —H | 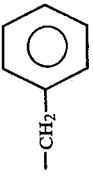 |
| 18 |  | —$CH_3$ | —H | —$C(CH_3)_3$ | one | —H |  |
| 19 |  |  | —H | —$C_2H_5$ | zero | —H |  |

-continued

| Ex. | R₄ | R₁ | R₂ | R₃ | n | R₅ | X |
|---|---|---|---|---|---|---|---|
| | | Col. I $R_4-\overset{O}{\overset{\|}{C}}-\overset{R_2}{\overset{\|}{CH}}-\overset{R_5}{\overset{\|}{CH}}-\overset{O}{\overset{\|}{P}}-(CH_2)_n-\overset{R_5}{\overset{\|}{CH}}-COOH$ | | | Col. II HX | | | Col. III $R_4-\overset{O}{\overset{\|}{C}}-\overset{R_2}{\overset{\|}{CH}}-\overset{R_5}{\overset{\|}{CH}}-\overset{O}{\overset{\|}{P}}-(CH_2)_n-\overset{R_5}{\overset{\|}{CH}}-\overset{O}{\overset{\|}{C}}-X$ |
| 20 | furfuryl-CH₂– | –(CH₂)₂–C₆H₅ | –H | –CH₂–C₆H₅ | one | –H | 4-methoxy-piperidine-COOCH₂-C₆H₅ (L) |
| 21 | –C₆H₅ | –(CH₂)₂–C₆H₅ | –H | –C₂H₅ | zero | –CH₃ | 4-OC(CH₃)₃-piperidine-COOCH₂-C₆H₅ (L) |
| 22 | –C₆H₅ | –(CH₂)₂–C₆H₅ | –H | –C₂H₅ | zero | –H | 4-phenoxy-piperidine-COOCH₂-C₆H₅ (L) |
| 23 | –C₆H₅ | –(CH₂)₂–C₆H₅ | –H | –CH₂–C₆H₅ | zero | –H | 4-(4-fluorobenzyloxy)-piperidine-COOCH₂-C₆H₅ (L) |

-continued

| Ex. | Col. I  $R_4-\overset{O}{\overset{\|}{C}}-\overset{R_2}{\overset{\|}{C}H}-\overset{O}{\overset{\|}{C}H}-\overset{O}{\overset{\|}{P}}-(CH_2)_n-\overset{R_5}{\overset{\|}{C}H}-COOH$ |  |  | Col. II  HX |  | Col. III  $R_4-\overset{O}{\overset{\|}{C}}-\overset{R_2}{\overset{\|}{C}H}-\overset{O}{\overset{\|}{C}H}-\overset{O}{\overset{\|}{P}}-(CH_2)_n-\overset{R_5}{\overset{\|}{C}H}-\overset{O}{\overset{\|}{C}}-X$ |  |
|---|---|---|---|---|---|---|---|
|  | $R_4$ | $R_1$ | $R_2$ | $R_3$ |  | $n$ | $R_5$ | $X$ |
| 24 | ◯ | ◯—(CH$_2$)$_2$— | —H | —C$_2$H$_5$ |  | zero | —H | [structure with biphenylether, —N—, COOCH$_2$—◯, (L)] |
| 25 | ◯ | ◯—(CH$_2$)$_2$— | —H | —C$_2$H$_5$ |  | one | —H | [structure with SCH$_3$, —N—, COOCH$_2$—◯, (L)] |
| 26 | ◯ | ◯—(CH$_2$)$_3$— | —H | —CH$_2$—◯ |  | zero | —CH$_3$ | [structure with SC$_2$H$_5$, —N—, COOCH$_2$—◯, (L)] |
| 27 | ◯—(CH$_2$)$_5$— | ◯—(CH$_2$)$_2$— | —H | —C$_2$H$_5$ |  | zero | —H | [structure with 4-F-phenyl-S—, —N—, COOCH$_2$—◯, (L)] |

-continued

| Ex. | R$_4$ | R$_1$ | R$_2$ | R$_3$ | n | R$_5$ | X |
|---|---|---|---|---|---|---|---|
| | | Col. I $R_4-C(=O)-CH(R_2)-CH(R_1)-P(=O)(OR_3)-(CH_2)_n-CH(R_5)-COOH$ | | Col. II HX | | | Col. III $R_4-C(=O)-CH(R_2)-CH(R_1)-P(=O)(OR_3)-(CH_2)_n-CH(R_5)-C(=O)-X$ |
| 28 | Ph-(CH$_2$)$_4$- | Ph- | -CF$_3$ | -C$_2$H$_5$ | zero | -H | PhS-CH$_2$-CH(-)-CH$_2$-N(L)(COOCH$_2$Ph) |
| 29 | 4-HO-Ph- | Ph-(CH$_2$)$_2$- | -H | -CH$_2$-Ph | zero | -H | (naphthyl-2-S)-CH(-)-CH$_2$-N(L)(COOCH$_2$Ph) |
| 30 | Ph- | Ph-(CH$_2$)$_2$- | -CH$_3$ | -C$_2$H$_5$ | one | -CH$_3$ | (thiophene-2-CH$_2$)-CH(-)-CH$_2$-N(L)(COOCH$_2$Ph) |
| 31 | Ph- | Ph-(CH$_2$)$_2$- | -H | -C$_2$H$_5$ | zero | -H | (4-CH$_3$O-Ph-S)-CH(-)-CH$_2$-N(L)(COOCH$_2$Ph) |

-continued

| | Col. I | | | Col. II | Col. III | | |
|---|---|---|---|---|---|---|---|
| | $R_4-\overset{O}{\underset{}{C}}-CH-\underset{R_1}{\overset{R_2}{CH}}-\overset{O}{\underset{OR_3}{P}}-(CH_2)_n-\overset{R_5}{\underset{}{CH}}-COOH$ | | | HX | $R_4-\overset{O}{\underset{}{C}}-CH-\underset{R_1}{\overset{R_2}{CH}}-\overset{O}{\underset{OR_3}{P}}-(CH_2)_n-\overset{R_5}{\underset{}{CH}}-\overset{O}{\underset{}{C}}-X$ | | |
| Ex. | $R_4$ | $R_1$ | $R_2$ | $R_3$ | n | $R_5$ | X |
| 32 | $H_3C-$ | $-(CH_2)_2-C_6H_5$ | $-H$ | $-C_2H_5$ | zero | $-H$ | $-N(CF_2F)-CH(COOCH_2C_6H_5)$ (L) |
| 33 | $H_3C-(CH_2)_3-$ | $-(CH_2)_2-C_6H_5$ | $-H$ | $-C_2H_5$ | zero | $-H$ | $-N(C(OCH_3)(OCH_3))-CH(COOCH_2C_6H_5)$ (L) |
| 34 | $C_6H_5-$ | $-(CH_2)_2-C_6H_5$ | $-H$ | $-CH_2C_6H_5$ | zero | $-H$ | $-N(\text{dithiane})-CH(COOCH_2C_6H_5)$ (L) |
| 35 | $C_6H_5-$ | $-(CH_2)_2-C_6H_5$ | $-H$ | $-C_2H_5$ | zero | $-H$ | $-N(\text{methyl dioxolane})-CH(COOCH_2C_6H_5)$ (L) |

-continued

| Ex. | R4 | Col. I<br>$R_4-\overset{O}{\overset{\|}{C}}-\overset{R_2}{\overset{\|}{C}H}-\overset{}{\overset{\|}{C}H}-\overset{O}{\overset{\|}{P}}-(CH_2)_n-\overset{R_5}{\overset{\|}{C}H}-COOH$<br>R1 OR3 | | | Col. II<br>HX<br>R3 | Col. III<br>$R_4-\overset{O}{\overset{\|}{C}}-\overset{R_2}{\overset{\|}{C}H}-\overset{}{\overset{\|}{C}H}-\overset{O}{\overset{\|}{P}}-(CH_2)_n-\overset{R_5}{\overset{\|}{C}H}-\overset{O}{\overset{\|}{C}}-X$<br>R1 OR3 | | |
|---|---|---|---|---|---|---|---|---|
| | | R1 | R2 | | | n | R5 | X |
| 36 |  |  | —H | | —C2H5 | zero | —H |  |
| 37 | 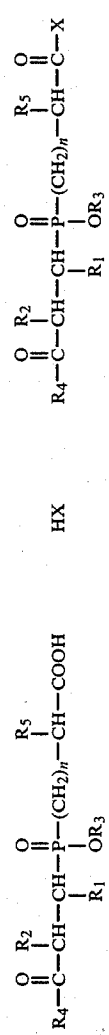 |  | —H | | —C(CH3)3 | zero | —H |  |
| 38 |  |  | —H | |  | zero | —CH3 |  |
| 39 | 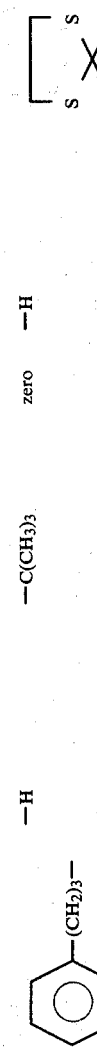 |  | —H | | —C2H5 | zero | —H |  |

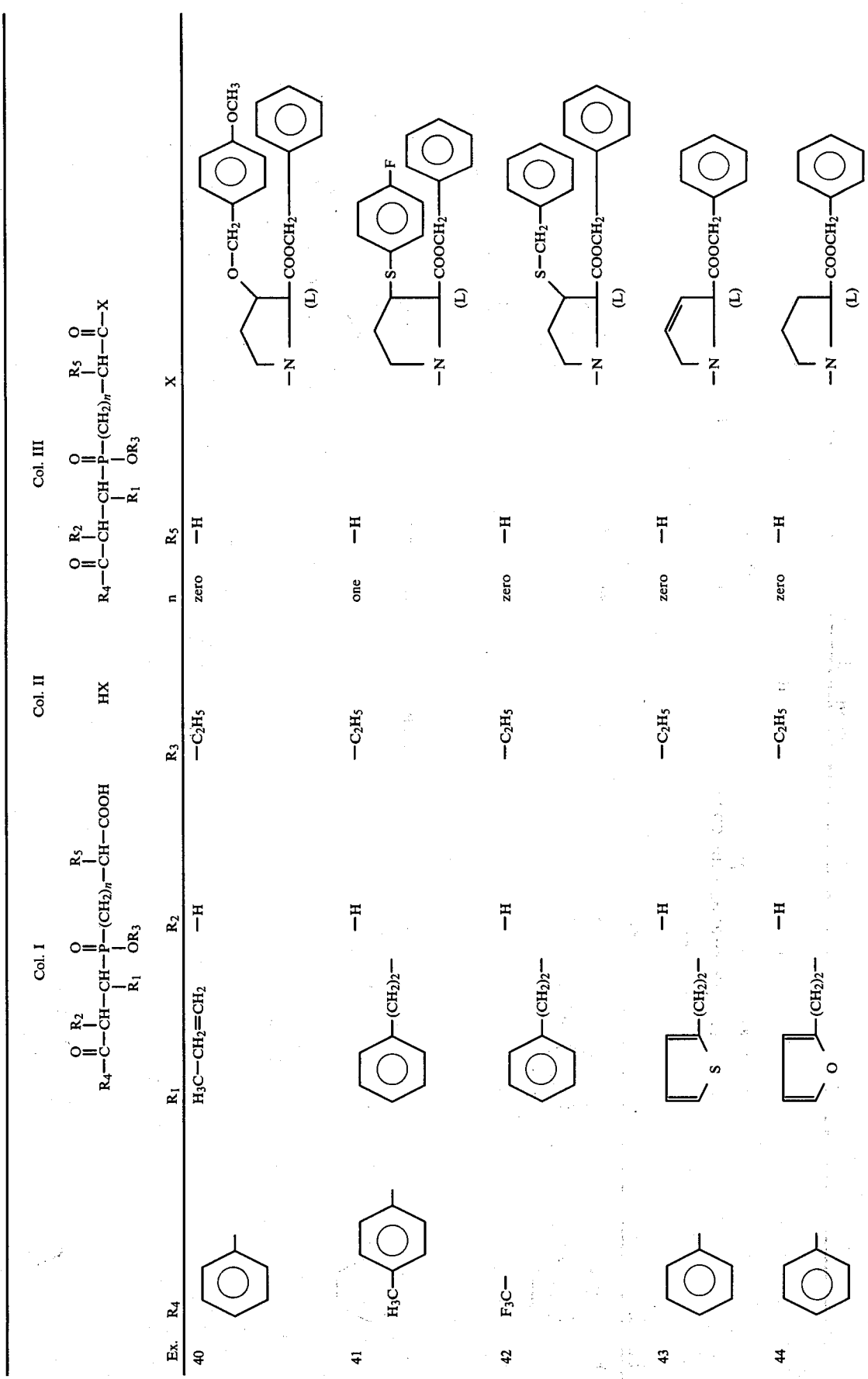

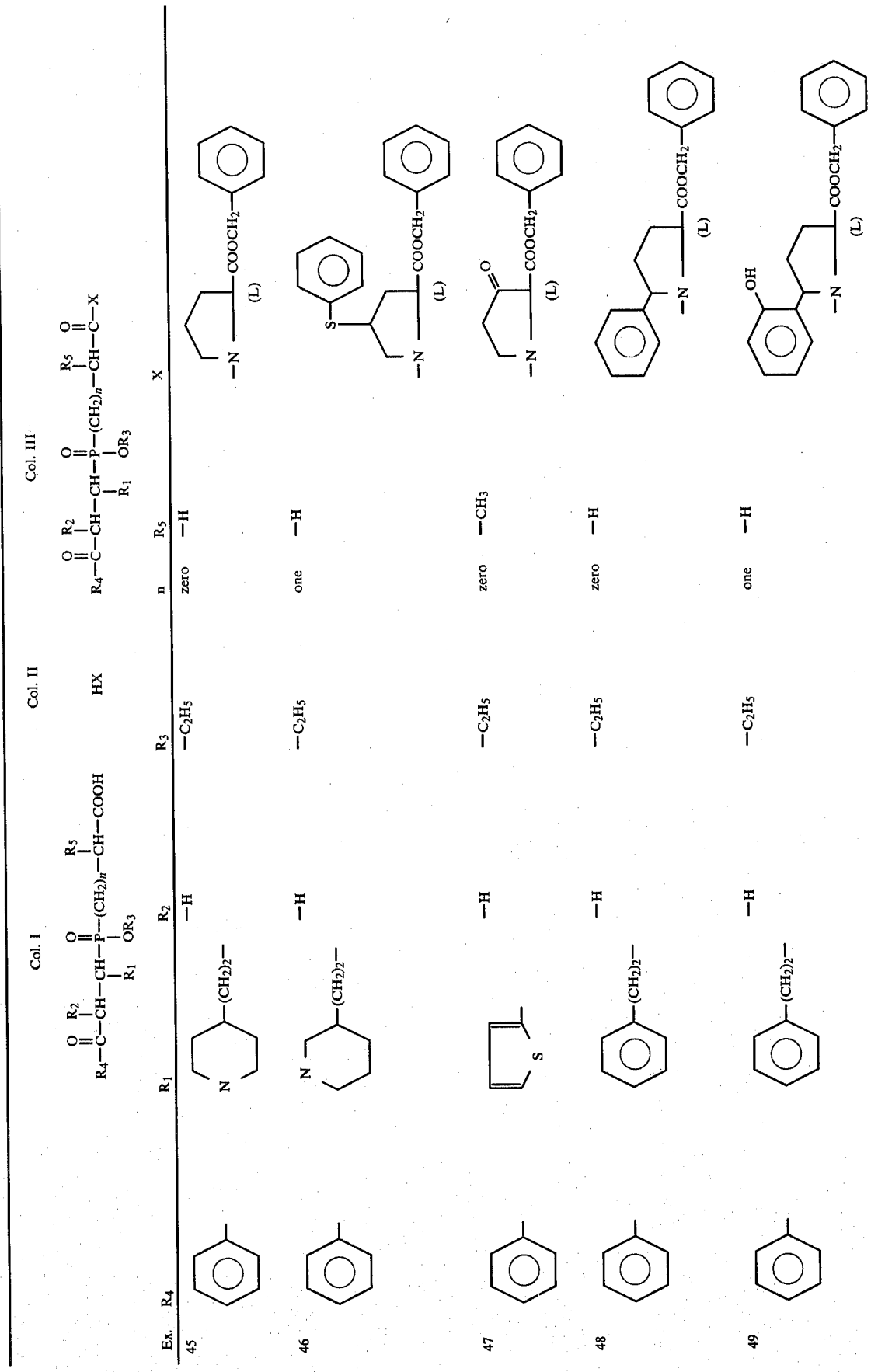

-continued

| | Col. I $R_4-\overset{O}{\overset{\|}{C}}-\overset{R_2}{\overset{\|}{CH}}-\overset{R_5}{\overset{\|}{CH}}-\overset{O}{\overset{\|}{P}}-(CH_2)_n-\overset{R_5}{\overset{\|}{CH}}-COOH$ | | | Col. II HX | Col. III $R_4-\overset{O}{\overset{\|}{C}}-\overset{R_2}{\overset{\|}{CH}}-\overset{R_1}{\overset{\|}{CH}}-\overset{O}{\overset{\|}{P}}-(CH_2)_n-\overset{R_5}{\overset{\|}{CH}}-\overset{O}{\overset{\|}{C}}-X$ | | |
|---|---|---|---|---|---|---|---|
| Ex. | $R_4$ | $R_1$ | $R_2$ | $R_3$ | n | $R_5$ | X |
| 50 | 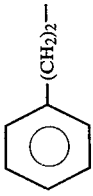 | 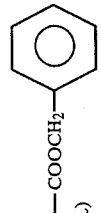 | —H | —C$_2$H$_5$ | zero | —CH$_3$ | 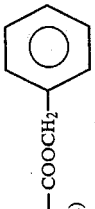 |
| 51 |  | 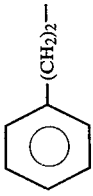 | —H | —C$_2$H$_5$ | zero | —H | 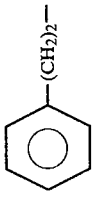 |
| 52 |  |  | —H | —C$_2$H$_5$ | zero | —H | 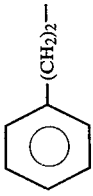 |
| 53 | 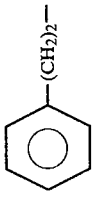 |  | —H | —CH$_2$—  | zero | —H | 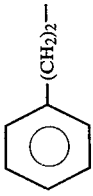 |
| 54 | 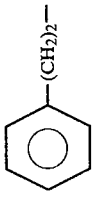 |  | —H | —CH$_2$—  | zero | —H | 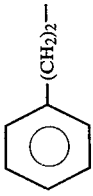 |

-continued

| Ex. | Col. I  $R_4-\overset{O}{C}-CH-\overset{R_2}{CH}-\overset{O}{P}-(CH_2)_n-\overset{R_5}{CH}-COOH$ $\phantom{R_4-C-CH-}R_1\phantom{-P-}OR_3$ | | | | Col. II HX | Col. III $R_4-\overset{O}{C}-CH-\overset{R_2}{CH}-\overset{O}{P}-(CH_2)_n-\overset{R_5}{CH}-\overset{O}{C}-X$ $\phantom{R_4-C-CH-}R_1\phantom{-P-}OR_3$ | | |
|---|---|---|---|---|---|---|---|---|
| | $R_4$ | $R_1$ | $R_2$ | $R_3$ | | n | $R_5$ | X |
| 55 | $C_6H_5CH_2-$ | $C_6H_5(CH_2)_3-$ | —H | $-C_2H_5$ | | zero | —H | pyrrolidine-N-COOCH$_2$C$_6$H$_5$ (L) |
| 56 | $C_6H_5CH_2-$ | $C_6H_5(CH_2)_3-$ | —H | $-C_2H_5$ | | zero | —H | 3-phenyl-pyrrolidine-N-COOCH$_2$C$_6$H$_5$ (L) |
| 57 | $C_6H_5CH_2-$ | $C_6H_5(CH_2)_3-$ | —H | $-C_2H_5$ | | zero | —H | 1,3-dithiolane-pyrrolidine-N-COOCH$_2$C$_6$H$_5$ (L) |
| 58 | 4-F-C$_6$H$_4$-CH$_2$- | $C_6H_5(CH_2)_2-$ | —H | $-CH_2C_6H_5$ | | zero | —H | pyrrolidine-N-COOCH$_2$C$_6$H$_5$ (L) |
| 59 | 4-H$_3$CO-C$_6$H$_4$-CH$_2$- | $C_6H_5(CH_2)_2-$ | —H | $-C_2H_5$ | | zero | —H | pyrrolidine-N-COOCH$_2$C$_6$H$_5$ (L) |

-continued

| | Col. I $R_4-\overset{O}{\overset{\|}{C}}-CH-\underset{\underset{R_1}{\|}}{CH}-\overset{\overset{O}{\|}}{P}-(CH_2)_n-CH-COOH$ | | | Col. II HX | | Col. III $R_4-\overset{O}{\overset{\|}{C}}-CH-\underset{\underset{R_1}{\|}}{CH}-\overset{\overset{O}{\|}}{P}-(CH_2)_n-CH-\overset{\overset{O}{\|}}{C}-X$ | | |
|---|---|---|---|---|---|---|---|---|
| Ex. | $R_4$ | $R_1$ | $R_2$ | $R_3$ | n | $R_5$ | X |
| 60 | ⌬ | —H | —(CH$_2$)$_2$—⌬ | —C$_2$H$_5$ | zero | —H | —N⟨(CH$_2$)$_3$⟩CH-COOCH$_2$-⌬ (L) |
| 61 | ⌬ | —H | —(CH$_2$)$_3$—⌬ | —C$_2$H$_5$ | zero | —H | —N⟨(CH$_2$)$_3$⟩CH-COOCH$_2$-⌬ (L) |
| 62 | ⌬-CH$_2$— | —H | —(CH$_2$)$_2$—⌬ | —C$_2$H$_5$ | zero | —H | —N⟨(CH$_2$)$_2$-C(S)(S)⟩CH-COOCH$_2$-⌬ (L) |
| 63 | ⌬-CH$_2$— | —(CH$_2$)$_2$—⌬ | —H | —C$_2$H$_5$ | zero | —H | —N⟨(CH$_2$)$_3$⟩CH-COOCH$_2$OCOCH$_3$ |
| 64 | ⌬-CH$_2$— | —(CH$_2$)$_3$—⌬ | —H | —C$_2$H$_5$ | zero | —CH$_3$ | —N⟨(CH$_2$)$_3$⟩CH-COOCH$_2$OCOC$_6$H$_5$ |
| 65 | ⌬-CH$_2$— | —(CH$_2$)$_3$—⌬ | —H | —C$_2$H$_5$ | zero | —H | —N⟨(CH$_2$)$_3$⟩CH-COO-(phthalidyl) |

-continued

| | Col. I  R₄—C(=O)—CH(R₂)—CH(R₁)—P(=O)(OR₃)—(CH₂)ₙ—CH(R₅)—COOH | | | Col. II  HX | Col. III  R₄—C(=O)—CH(R₂)—CH(R₁)—P(=O)(OR₃)—(CH₂)ₙ—CH(R₅)—C(=O)—X | | |
|---|---|---|---|---|---|---|---|
| Ex. | R₄ | R₁ | R₂ | R₃ | n | R₅ | X |
| 66 | 4-F-C₆H₄— | C₆H₅—(CH₂)₂— | —H | —C₂H₅ | one | —H | pyrrolidine substituted with —S—C₆H₅ and —COOCH₂OCOC(CH₃)₃ |
| 67 | 4-H₃CO-C₆H₄-CH₂— | —H | C₆H₅—(CH₂)₂— | —C₂H₅ | zero | —H | pyrrolidine substituted with —CH₂—C₆H₅ and —COOCH₂OCOC₂H₅ |
| 68 | C₆H₅— | C₆H₅—(CH₂)₂— | —H | —CH₂—C₆H₅ | zero | —H | piperidine substituted with —COOCH(CH₃)OCOC(CH₃)₃ |

Reduction of the product of Example 10 yields the corresponding 4-amino product.

EXAMPLE 69

(±)-1-[[[(2,2-Dimethyl-1-oxopropoxy)methoxy][3-oxo-3-phenyl-1-(2-phenylethyl)propyl]-phosphinyl]acetyl]-L-proline (a) (±)-1-[[Ethoxy[3-oxo-3-phenyl-1-(2-phenylethyl)propyl]phosphinyl]acetyl]-L-proline, 1,1-dimethylethyl ester Substitution of L-proline, 1,1-dimethyl ester for the L-proline, benzyl ester in Example 1(e) yields (±)-1-[[ethxy[3-oxo-3-phenyl-1-(2-phenylethyl)propyl]phosphinyl]acetyl]-L-proline, 1,1-dimethylethyl ester.

(b) (±)-1-[Hydroxy[3-oxo-3-phenyl-1-(2-phenylethyl)propyl]phosphinyl]acetyl]-L-proline, 1,1-dimethylethyl ester Substitution of the product of part (a) for the (±)-1-[[ethoxy[3-oxo-3-phenyl-1-(2-phenylethyl)propyl]phosphinyl]acetyl]-L-proline, phenylmethyl ester in Example 1 (f) yields (±)-1-[[hydroxy[3-oxo-3-phenyl-1-(2-phenylethyl)propyl]phosphinyl]acetyl]-L-proline, 1,1-dimethylethyl ester.

(c) (±)-1-[[[(2,2-Dimethyl-1-oxopropoxy)methoxy][3-oxo-3-phenyl-1-(2-phenylethyl)propyl]phosphinyl]acetyl]-L-proline, 1,1-dimethyl ester An equimolar mixture of triethylamine and chloromethyl pivalate are added to a solution of (±)-1-[[hydroxy[3-oxo-3-phenyl-1-(2-phenyl-ethyl)propyl]phosphinyl]acetyl]-L-proline, 1,1-dimethyl ester from part (b) in dimethylformamide under an argon atmosphere. The mixture is stirred under an argon atmosphere. The mixture is stirred for several hours at room temperature, diluted with ethyl acetate, washed with water, brine, dried (MgSO$_4$), and evaporated. The crude product is chromatographed to give (±)-1-[[[(2,2-dimethyl-1-oxopropoxy)methoxy][3-oxo-3-phenyl-1-(2-phenylethyl)propyl]phosphinyl]acetyl]-L-proline, 1,1-dimethyl ester.

(d) (±)-1-[[[(2,2-Dimethyl-1-oxopropyl)methoxy][3-oxo-3-phenyl-1-(2-phenylethyl)propyl]phosphinyl]acetyl]-L-proline A solution of the diester product from part (c) in CH$_2$Cl$_2$ is added to trifluoroacetic acid containing 10% anisole and stirred for one hour. The reaction mixture is concentrated and the residue triturated repeatedly with ether and hexane. The crude product is chromatographed on silica gel to yield (±)-1-[[[(2,2-dimethyl-1-oxopropoxy)methoxy][3-oxo-3-phenyl-1-(2-phenylethyl)propyl]phosphinyl]acetyl]-L-proline.

EXAMPLES 70–74

Following the procedure of Example 69 but employing the alkylating agent shown in Col. I for the chloromethyl pivalate, one obtains the product listed in Col. II.

| Example | Col. I | Col. II |
|---|---|---|
| 70 | Br—CH$_2$—O—C(=O)—CH$_3$ | (±)-1-[[[(acetyloxy)methoxy][3-oxo-3-phenyl-1-(2-phenylethyl)-propyl]-phosphinyl]acetyl]-L-proline |
| 71 | Cl—CH$_2$—O—C(=O)—OC$_2$H$_5$ | (±)-1-[[[(ethoxycarbonyloxy)methoxy][3-oxo-3-phenyl-1-(2-phenylethyl)propyl]phosphinyl]acetyl]-L-proline |
| 72 | Br-substituted phthalide (3-bromo-1(3H)-isobenzofuranone) | (±)-1-[[(1,3-dihydro-3-oxo-1-isobenzofuranyloxy)[3-oxo-3-phenyl-1-(2-phenylethyl)propyl]phosphinyl]acetyl]-L-proline |
| 73 | ClCH$_2$O—C(=O)—C$_6$H$_5$ | (±)-1-[[[(benzoyloxy)methoxy][3-oxo-3-phenyl-1-(2-phenylethyl)propyl]-phosphinyl]acetyl]-L-proline |
| 74 | Cl—CH(CH$_3$)—O—C(=O)—CH$_3$ | (±)-1-[[[1-(acetyloxy)ethoxy][3-oxo-3-phenyl-1-(2-phenylethyl)propyl]-phosphinyl]acetyl]-L-proline |

Similarly, the alkylating agents of Examples 69 to 74 can be employed with ester products of Examples 4 to 62 to yield other compounds within the scope of this invention.

EXAMPLE 75

1000 tablets each containing the following ingredients:

| | |
|---|---|
| (±)-1-[[Hydroxy[3-oxo-3-phenyl-1-(2-phenylethyl)-propyl]phosphinyl]acetyl]-L-proline, dilithium salt | 100 mg. |
| Corn starch | 50 mg. |
| Gelatin | 7.5 mg. |
| Avicel (microcrystalline cellulose) | 25 mg. |
| Magnesium stearate | 2.5 mg. |
| | 185 mg. | are prepared from sufficient bulk quantities by mixing (±)-1-[[hydroxy[3-oxo-3-phenyl-1-(2-phenylethyl)-propyl]phosphinyl]acetyl]-L-proline, dilithium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 74 can be prepared.

EXAMPLE 76

1000 tablets each containing the following ingredients:

| | |
|---|---|
| (±)-1-[[Hydroxy[1-(2-oxo-2-phenylethyl)heptyl]phosphinyl]acetyl]-L-proline, dilithium salt | 50 mg. |
| Lactose | 25 mg. |
| Avicel | 38 mg. |
| Corn starch | 15 mg. |
| Magnesium stearate | 2 mg. |
| | 130 mg. | are prepared from sufficient bulk quantities by mixing the (±)-1-[[hydroxy[1-(2-oxo-2-phenylethyl) heptyl]-phosphinyl]acetyl]-L-proline, dilithium salt, lactose, and Avicel and then blending with the corn starch. Magnesium stearate is added and the dry mixture is compressed in a tablet press to form 100 tablets each containing 50 mg. of active ingredient. The tablets are coated with a solution of Methocel E 15 (methyl cellulose) including as a color a lake containing yellow #6.

In a similar manner, tablets containing 50 mg. of the product of any of Examples 1 and 3 to 74 can be prepared.

EXAMPLE 77

Two piece #1 gelatin capsules each containing 100 mg. (±)-1-[[hydroxy[3-oxo-1-(2-phenylethyl)-octyl]-phosphinyl]acetyl]-L-proline are filled with a mixture of the following ingredients:

| | |
|---|---|
| (±)-1-[[Hydroxy[3-oxo-1-(2-phenylethyl)octyl]phosphinyl]acetyl]-L-proline | 100 mg. |
| Magnesium stearate | 7 mg. |
| Lactose | 193 mg. |

In a similar manner, capsules containing 100 mg. of the product of any of Examples 1, 2, and 4 to 74 can be prepared.

EXAMPLE 78

1000 tablets each containing the following ingredients:

| | |
|---|---|
| (±)-1-[[Hydroxy[3-oxo-3-phenyl-1-(2-phenylethyl)-propyl]phosphinyl]acetyl]-L-proline | 100 mg. |
| Avicel | 100 mg. |
| Hydrochlorothiazide | 12.5 mg. |
| Lactose | 113 mg. |
| Corn starch | 17.5 mg. |
| Stearic acid | 7 |
| | 350 mg. | are prepared from sufficient bulk quantities by slugging the (±)-1-[[hydroxy[3-oxo-3-phenyl-1-(2-phenylethyl)-propyl]phosphinyl]acetyl]-L-proline, Avicel and a portion of the stearic acid. The slugs are ground and passed through a #2 screen, then mixed with the hydrochlorothiazide, lactose, corn starch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 2 to 74.

What is claimed is:

1. A compound of the formula $$R_4-\overset{O}{\underset{}{C}}-\overset{R_2}{\underset{R_1}{CH}}-\overset{}{\underset{}{CH}}-\overset{O}{\underset{OR_3}{P}}-(CH_2)_n-\overset{R_5}{\underset{}{CH}}-\overset{O}{\underset{}{C}}-OH$$

wherein n is zero or one;

R$_5$ is hydrogen, lower alkyl, halo substituted lower alkyl, benzyl, or phenethyl;

R$_3$ is hydrogen, lower alkyl, benzyl, or benzhydryl;

R$_4$ is hydrogen, lower alkyl, halo substituted lower alkyl,

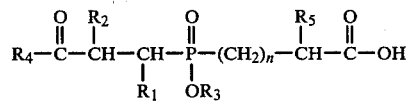

cycloalkyl, 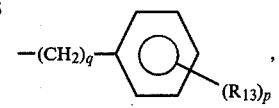,

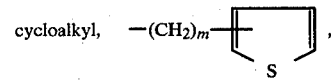

R$_1$ and R$_2$ are independently selected from the group consisting of hydrogen, lower alkyl, halo substituted lower alkyl,

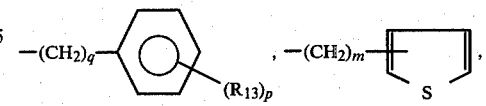

-continued $-(CH_2)_m-$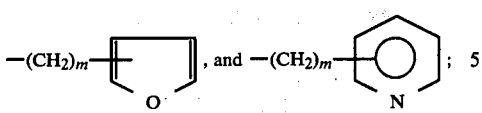, and $-(CH_2)_m-$ ;

$R_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;

q is zero or an integer from 1 to 7;

m is zero, one, two or three; and p is one, two or three provided that p is more than one only if $R_{13}$ is hydrogen, methyl, methoxy, chloro, or fluoro.

2. A compound of claim 1 wherein n is zero;

$R_2$ is hydrogen; and $R_5$ is hydrogen.

3. A compound of claim 2 wherein $R_4$ is lower alkyl of 1 to 7 carbons, trifluoromethyl,

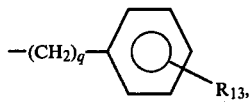

cyclopentyl, cyclohexyl,

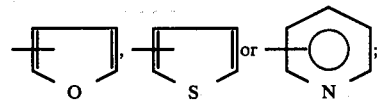

$R_3$ is hydrogen, lower alkyl, or benzyl;

$R_1$ is lower alkyl of 1 to 7 carbons, or

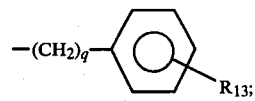

q is zero or an integer from 1 to 4; and $R_{13}$ is hydrogen, methyl, methoxy, methylthio, chloro, bromo, fluoro, or hydroxy.

4. The compound of claim 3 wherein $R_4$ is phenyl; $R_1$ is

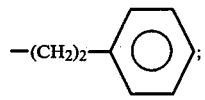

and $R_3$ is $-C_2H_5$.

5. The compound of claim 3 wherein $R_4$ is phenyl; $R_1$ is $-(CH_2)_5-CH_3$; and $R_3$ is $-C_2H_5$.

6. The compound of claim 3 wherein $R_4$ is $-(CH_2)_4-CH_3$; $R_1$ is

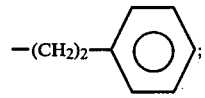

and $R_3$ is $-C_2H_5$.

* * * * *

UNITED STATES PATENT AND TRADEMARK OFFICE
CERTIFICATE OF CORRECTION

PATENT NO. : 4,416,833                Page 1 of 2
DATED      : November 22, 1983
INVENTOR(S): Donald S. Karanewsky et al.

It is certified that error appears in the above-identified patent and that said Letters Patent are hereby corrected as shown below:

Column 4, line 29, after are should be inserted -- $-(CH_2)_2-$, --
Column 6, line 36, before the formula should be inserted
-- (IV) --.
Column 14, line 59, delete "phosphenyl" and insert
-- phosphinyl --.
Column 33, Example 31, under $R_4$ the formula should read --

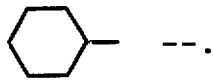 --.

Column 39, Example 40 the formula under $R_1$ should read
-- $H_3C-CH_2-CH_2$ --.
Column 41, Example 45 the formula under $R_1$ should read --

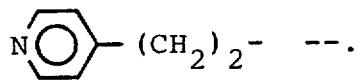 --.

UNITED STATES PATENT AND TRADEMARK OFFICE
CERTIFICATE OF CORRECTION

PATENT NO. : 4,416,833
DATED : November 22, 1983
INVENTOR(S) : Donald S. Karanewsky et al.

It is certified that error appears in the above-identified patent and that said Letters Patent are hereby corrected as shown below:

Column 41, Example 46, the formula under $R_1$ should read

--  --.

Column 45, Example 56, the top portion of the formula should read

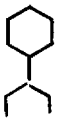

Column 52, line 9, delete "oxopropyl)" and insert -- oxopropoxy) --.

Column 52, Example 70, under Col. I, delete "(±)-1-[[[(acetoxy)-methoxy][3-oxo-3-phenyl-1-(2-phenylethyl)-propyl]-phosphinyl]-acetyl]-L-proline".

Column 52, Example 70 under Col. II, insert --
(±)-1-[[[(acetyloxy)methoxy][3-oxo-3-phenyl-1-(2-phenylethyl)-propyl]phosphinyl]acetyl]-L-proline -- .

Signed and Sealed this

Third Day of December 1985

[SEAL]

Attest:

DONALD J. QUIGG

*Attesting Officer*   *Commissioner of Patents and Trademarks*